United States Patent [19]

Wade

[11] Patent Number: 5,904,483
[45] Date of Patent: May 18, 1999

[54] DENTAL IMPLANT SYSTEMS AND METHODS

[76] Inventor: Curtis K. Wade, 2120 Dellesta Dr., Bellingham, Wash. 98226

[21] Appl. No.: 08/748,364

[22] Filed: Nov. 13, 1996

Related U.S. Application Data

[60] Provisional application No. 60/000,955, Nov. 17, 1995.
[51] Int. Cl.⁶ ........................................... A61C 8/00
[52] U.S. Cl. ................................. 433/173; 433/214
[58] Field of Search .................... 433/173, 174, 433/214

[56] References Cited

U.S. PATENT DOCUMENTS

| | | | |
|---|---|---|---|
| 4,290,755 | 9/1981 | Scott | 433/173 |
| 4,854,872 | 8/1989 | Detsch | 433/173 |
| 4,856,994 | 8/1989 | Lazzara et al. | 433/174 |
| 5,108,288 | 4/1992 | Perry | 433/174 |
| 5,125,839 | 6/1992 | Ingber et al. | 433/169 |
| 5,195,891 | 3/1993 | Sulc | 433/173 |
| 5,213,500 | 5/1993 | Salazar et al. | 433/173 |
| 5,238,405 | 8/1993 | Marlin | 433/172 |
| 5,302,126 | 4/1994 | Wimmer et al. | 433/173 |
| 5,417,570 | 5/1995 | Zuest et al. | 433/173 |
| 5,431,567 | 7/1995 | Daftary | 433/172 |
| 5,527,183 | 6/1996 | O'Brien | 433/174 |
| 5,556,280 | 9/1996 | Pelak | 433/172 |
| 5,569,037 | 10/1996 | Moy et al. | 433/172 |
| 5,688,123 | 11/1997 | Meiers et al. | 433/214 |

FOREIGN PATENT DOCUMENTS

| | | | |
|---|---|---|---|
| 2119258 | 11/1983 | United Kingdom | 433/174 |

OTHER PUBLICATIONS

Branemark System, 1995 brochure, Nobelpharma USA, Inc.
ITI Dental Implant System advertisement.
Emergence Profile System, 3I Implant Innovations, 1993.
Dentsply Implant advertisement, 1995.

*Primary Examiner*—Ralph A. Lewis
*Attorney, Agent, or Firm*—Michael R. Schacht; Hughes & Schacht, P.S.

[57] ABSTRACT

A dental implant system having a temporary abutment made of plastic. An impression coping, also made of plastic, is attached to the temporary abutment using a snap fit. This snap fit obviates the need to remove the temporary abutment during the process of taking an impression of the mouth in the area around an implant. The cap may be provided for the temporary abutment that is attached thereto using the same snap fit mechanism. The snap fit mechanism comprises projections formed on one of the components and recesses formed on the other of the components, where the projections engage the recesses to maintain the components in a desired position relative to each other against incidental force. However, these components may be separated by deliberate application of manual force when required.

44 Claims, 9 Drawing Sheets

FIG. 1
FIG. 2
FIG. 3
FIG. 4
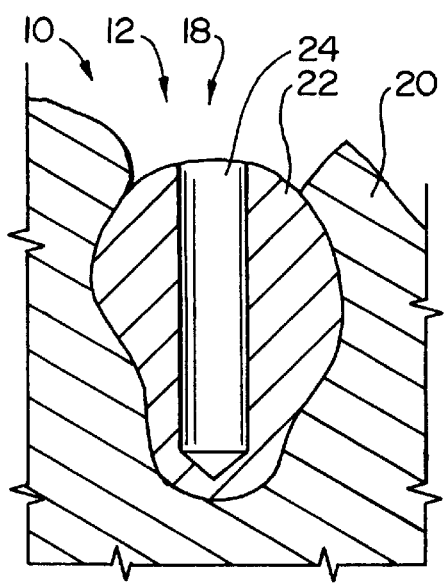
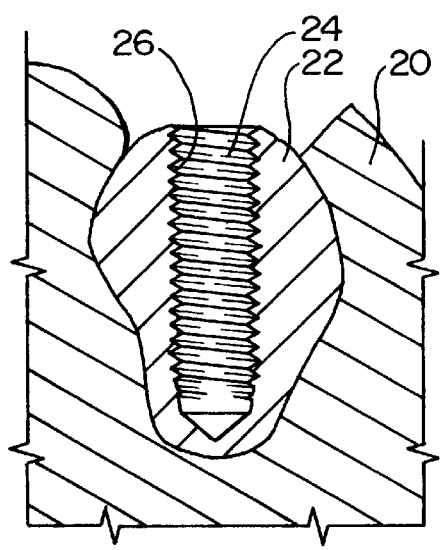
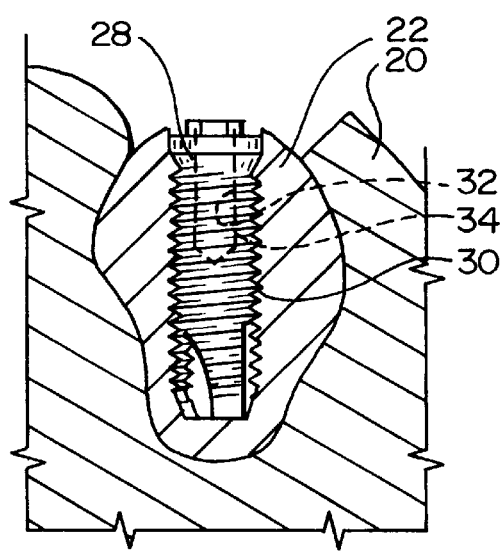
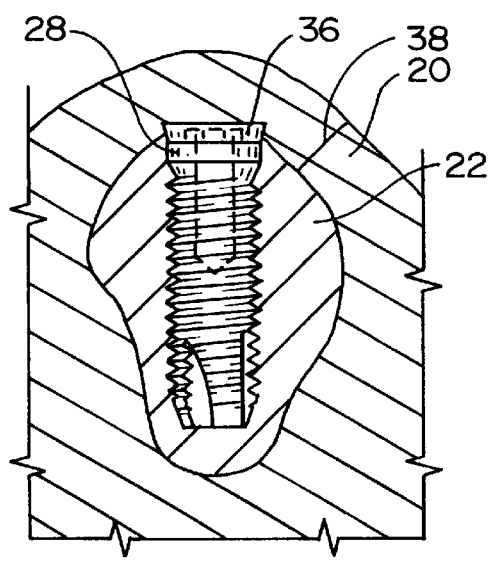

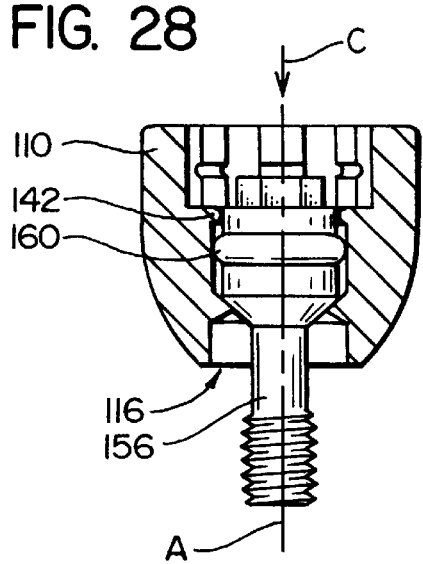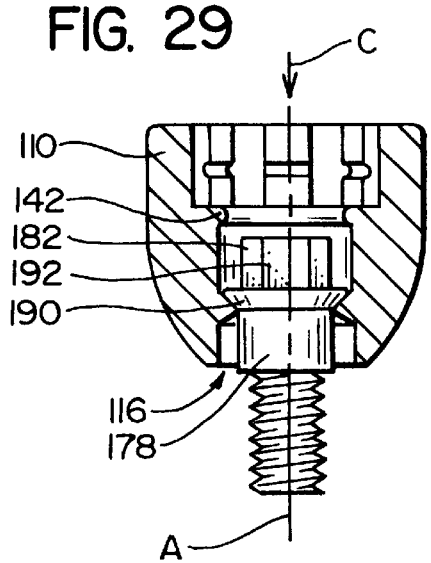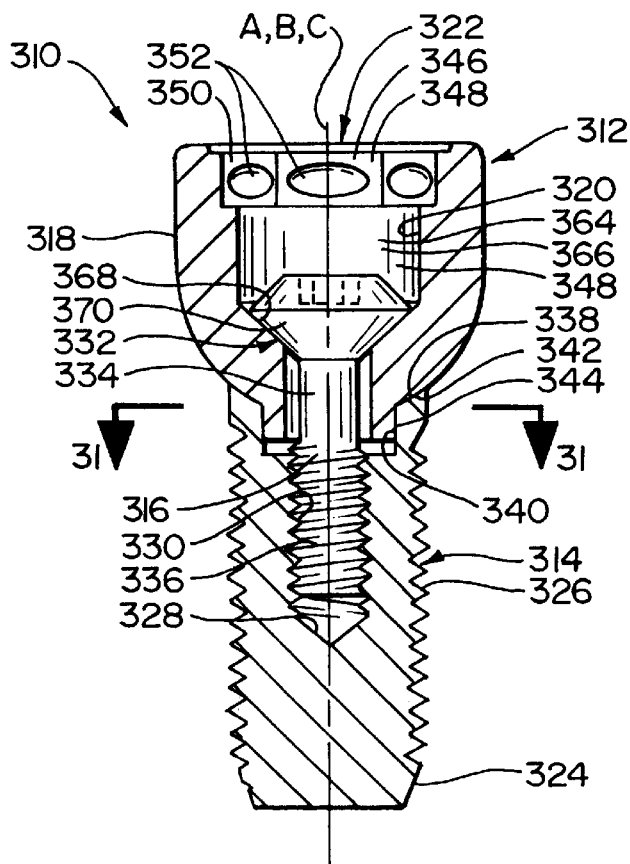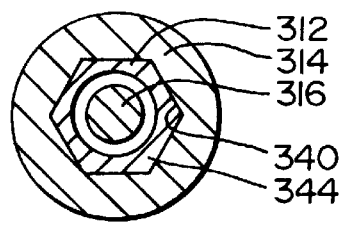

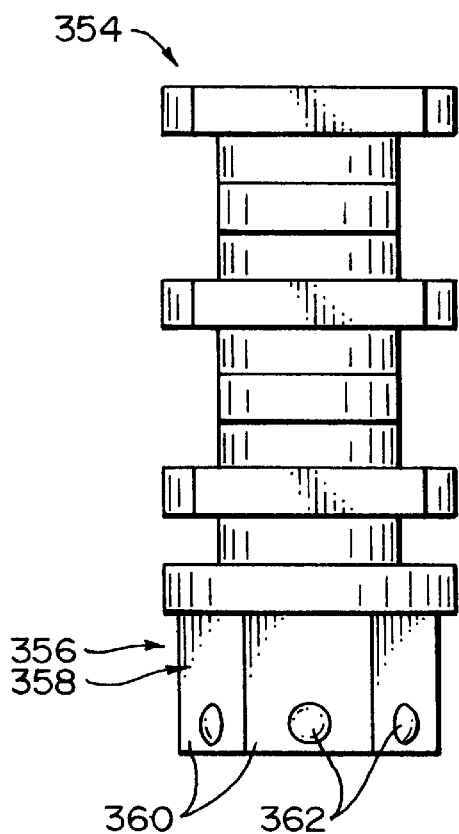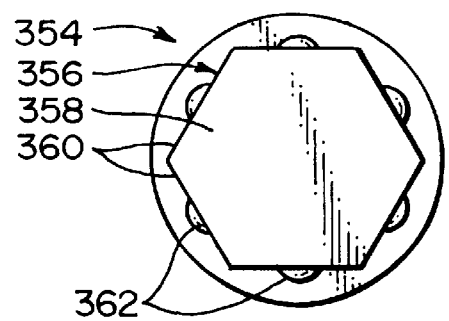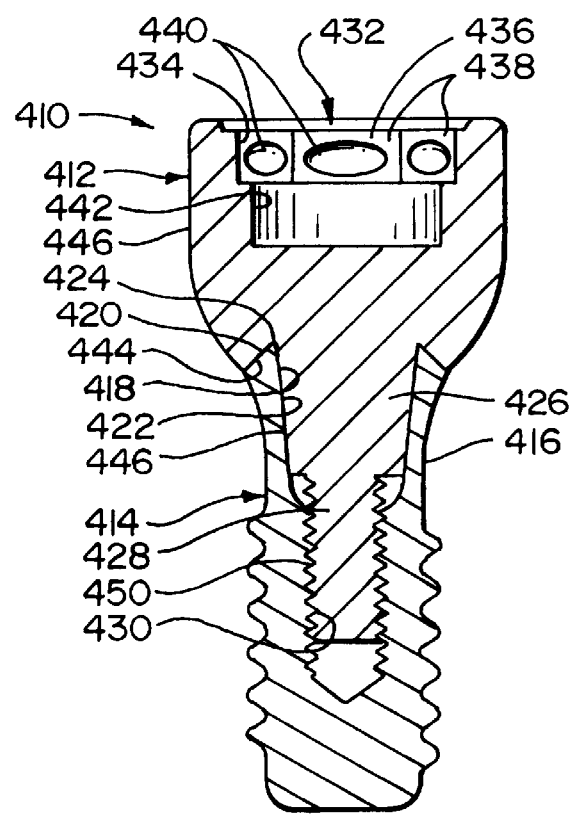

DENTAL IMPLANT SYSTEMS AND METHODS

RELATED APPLICATIONS

This application claims priority of U.S. Provisional patent application Ser. No. 60/006,955, which was filed on Nov. 17, 1995.

FIELD OF THE INVENTION

The present invention relates to prosthodontic methods and apparatus and, more specifically, to such methods and apparatus that simplify the making of dental impressions employed to fabricate a restorative tooth prosthesis.

BACKGROUND OF THE INVENTION

Many systems and methods are currently available for replacing lost teeth. These systems and methods comprise the following basic steps. First, an implant is threaded into a cavity formed in the patient's jaw at the location of a lost tooth. The implant is then allowed to osseointegrate with the jaw bone. A technician will then fabricate a prosthetic tooth on a permanent abutment member. The permanent abutment member is then attached to the implant to mount the prosthetic tooth at its appropriate location. In this context, the permanent abutment member forms the structural attachment between the prosthetic tooth and the implant, and the prosthetic tooth functionally and aesthetically replaces the exposed portion of the lost tooth.

It should be clear that this basic process can be employed when replacing a plurality of teeth as well as when replacing a single tooth. In the following discussion, the present invention is described in the context of replacing a single tooth; but one of ordinary skill in the art will recognize that the principles of the present invention are equally applicable to the replacement of more than one tooth at a time.

The step of fabricating the prosthetic tooth varies with the particular patient but requires that the position of the implant be captured so that the resulting prosthesis performs as required both functionally and aesthetically. If the position of the implant is not accurately captured, the resulting prosthesis may not function properly and may not look natural when attached to the implant.

The prosthesis fabrication process comprises the steps of taking an impression of the area of the lost tooth and, with the impression, forming a model of the area of the lost tooth. The process of taking the impression comprises the steps of attaching an impression coping to the implant, injecting hardenable impression material into the area surrounding the impression coping, and, when the impression material hardens, removing the impression material with the impression coping encased therein. To fabricate the model, an analog of the implant is then attached to the impression coping encased in the impression. Hardenable model material is then placed around the implant analog and allowed to harden. The model, with the implant analog buried therein, is then removed from the impression.

The position of the implant analog in the model should, and in most systems will, reflect the position of the implant in the mouth; that is, the model will contain surfaces corresponding to the surfaces of the teeth and soft tissue, with these model surfaces being accurately located relative to the implant analog. If the model accurately reflects the position of the implant in the mouth, a technician can accurately fabricate the prosthetic tooth in a laboratory setting.

While most currently available systems for replacing lost teeth allow the fabrication of a model that accurately reflects the position of the implant in the mouth, these systems each have drawbacks that, in general, result in the process of replacing lost teeth being fairly complicated and expensive.

To the Applicant's knowledge, all of the currently available systems and methods employ metal parts down to the implant during the process of taking the impression. Such metal parts are precision machined and thus relatively expensive. Although metal parts are in theory reusable, they must be sterilized between each use. And even if sterilized, these metal parts are often difficult to clean completely. Accordingly, in practice these parts are often discarded after being used once to eliminate the possibility of cross-contamination.

The use of metal parts also increases the complexity of previously available systems or methods for replacing lost teeth. More specifically, during the process of taking an impression and subsequently creating a model from that impression, it is necessary to temporarily join two components together (i.e., the impression coping is joined to the implant and the implant analog is joined to the impression coping). Using currently available systems, whenever two metal components are temporarily joined together, one of two methods must be used: (a) one of the components must be directly threaded onto the other; or (b) one of the components is internally threaded, the other component is unthreaded, and a separate screw engages the threaded component to attach the unthreaded component to the threaded component.

In the case where both of the components are threaded, one component is usually fixed and the other is rotated relative to the fixed component. For one component to be directly threaded onto another, one of these components must be freely rotatable relative to the other. For example, in certain systems, healing abutments are provided with a threaded post extending therefrom. To attach the healing abutment to the implant, the healing abutment is rotated relative to the implant such that the threaded post formed thereon is received within the threaded cavity defined by the implant.

Rotating one component relative to the other is not possible in many situations; for example, this is not possible when one of the components is an implant fixed within the mouth and the other is an impression coping fixed within an impression.

Accordingly, with previously available systems, the various components employed are attached to each other using threaded screws during the process of taking an impression and making a model therefrom. A screw is used to securely attach the impression coping to the implant while the impression material is injected around the impression coping. And a screw is also used to attach the implant analog to the impression coping during the process of making the model from the impression.

The use of screws to attach the impression coping onto the implant increases the complexity of the process of taking the impression. The dentist must thread the screw into the implant before the impression is taken and remove the screw from the implant to remove the impression from the mouth.

Another important drawback of prior art systems and methods of replacing teeth is that these systems commonly employ 20–30 components each having a specific purpose. Many of these components work only with a specific subset of other components.

In any case, all of the components of a given system must kept in inventory. And accurate records be kept to ensure that the oral surgeon, dentist, and laboratory technician all have the right parts at the right time. Further, because these components are small and many differ only in size, the difference between one component and another incompatible component may not be obvious to the naked eye, possibly resulting in confusion among various similar looking parts.

The fact that certain components work only with certain other components reduces the flexibility of the system. For example, in certain prior art systems, the permanent abutment member must be selected prior to the process of making the impression because a particular impression coping must be used for the selected permanent abutment. If, subsequently, the dentist or laboratory technician determines that another type of permanent abutment is more appropriate, a new impression with a different impression coping must be made.

RELATED ART

Perhaps the most common commercially available dental implant system is marketed by Branemark. The Branemark system employs a large number of metal components that are relatively expensive. Additionally, as generally discussed above, the dentist must decide at the time the impression is made what type of permanent abutment will be used to fabricated the prosthetic tooth. This reduces the flexibility of the overall process, because a new impression must be taken if it is later determined that a different type of permanent abutment member is more appropriate.

Branemark also markets a specialized single tooth dental implant system under the trade name CeraOne. The CeraOne process employs a titanium abutment that is attached to an implant after second stage surgery. This abutment has an elongate exposed portion that extends substantially above the gum line, and a flexible, synthetic polymer healing cover is placed over the abutment while the tissue heals after second stage surgery.

To take an impression using the CeraOne product, impression material is placed around the healing cover and allowed to harden. The impression is removed from the mouth, with the healing cover sliding off of the exposed elongate portion of the healing abutment.

The CeraOne product may be used to replace only a single tooth; the cover that slips on and off of the elongate projection on the healing abutment prevents an impression being taken of more than one implant because the implants are normally not parallel. The covers would not be able to slip off the non-parallel projections on the healing abutments. And in practice, this cover is typically not used while the gum tissue is allowed to heal after second stage surgery because the material from which it is made tends to absorb odors and become unclean even during this relatively short period.

A third type of relevant dental implant system is marketed by 3I under the trade name EPS. The EPS system is similar to the Branemark system in that it uses a large number of metal components. The EPS system is also typical in that members such as healing abutments or caps are threaded to allow them to be directly attached to the implant. And the EPS system employs a separate screw to attach impression copings and permanent abutments onto the implant.

The need thus exists for dental implant systems and methods that are simple to implement, allow the dental professional flexibility in the selection of permanent abutments, require fewer steps during fabrication of the prosthetic tooth, and are less expensive than those currently available on the marketplace.

OBJECTS OF THE INVENTION

From the foregoing, it should be apparent that one object of the present invention is to provide an improved systems and methods for replacing lost teeth.

Another more specific object of the present invention is to provide such methods and systems having a favorable mix of the following characteristics:

minimizes the use of expensive, precision milled components;

reduces the number of parts that must be kept on hand to implement such systems and methods;

employs low profile parts that allow a flapper to be worn after first and second stage surgery before the prosthetic tooth is permanently attached to the implant;

simplifies the process of taking an impression accurately captures the emergence profile of one or more implants in a patient's mouth;

delays the decision on which type of permanent abutment will be used to maintain for as long as possible flexibility in the selection of the permanent abutment member;

allows the use of techniques that are suitable for mass production resulting in components that may be discarded after a single use to prevent cross-contamination; and can be used with implants and permanent abutments currently available on the market.

SUMMARY OF THE INVENTION

These and other objects are obtained by the present invention, which is a system or method for replacing lost teeth. The present invention employs a temporary abutment that is attached to an implant member during second stage surgery. This temporary abutment member is left on the implant when the dentist makes an impression of the area of the mouth surrounding the implant. To capture the location of the implant, an impression feather is attached to the temporary abutment using a snap fit. The temporary abutment and impression coping are both made of plastic and one of these is provided with the projection and the other with an indentation. The projection engages the indentation when the impression coping is in the appropriate position relative to the temporary abutment and maintains the impression coping in this position throughout the process of injecting impression material around the impression coping.

When the impression material hardens, the entire impression may be simply lifted away from the implant. The snap fit that mounts the impression coping on to the temporary abutment is designed to allow manual removal of the impression coping, and thus the impression itself, from the implant.

From the foregoing description, it should be seen that the dentist does not need to remove the temporary abutment before making the impression. The dentist need only snap on the impression coping and make the impression. This significantly reduces the amount of time required to take an impression.

When the impression is delivered to the laboratory for the purpose of manufacturing a prosthetic tooth, a temporary abutment and analog of the insert are snap fit onto the exposed portion of the impression coping. Model material is then placed around the implant analog and allowed to harden. At this point, the model may be simply lifted away from the impression, with the snap fit formed between the temporary abutment attached to the implant analog and the impression coping easily being overcome by deliberate application of manual force.

The model thus contains an implant analog that captures the position of the implant in the mouth. The laboratory technician may then fabricate the prosthetic tooth on the model using conventional techniques.

Significantly, the decision on the type of permanent abutment that is to be used can be delayed until after the model has been made. This allows the laboratory technician flexibility in selecting an appropriate permanent abutment member even after the impression has been taken.

In the above example, the snap fit was described in the process of taking an impression of the location of an implant member in a mouth. The snap fit employed during this process may also be used for other components. For example, a cap may be attached to the temporary abutment during the healing period after the second stage surgery. Such a cap would prevent food and other debris form getting into the interior of the temporary abutment, but is easily removed by the dentist using readily available tools immediately prior to the attachment of the impression coping onto the temporary abutment.

Forming a temporary abutment out of plastic as described herein provides significant flexibility in the design of the temporary abutment member. This abutment member may thus be adapted to match an existing implant or permanent abutment currently on the market.

Also, the temporary abutment member may be mass produced using injection molding techniques. The preferable material for the plastic components used in this system is an acetyl copolymer. This material may be accurately injection molded, has sufficient rigidity to function as set forth above, is durable, and is biocompatible.

A dental implant system or method constructed in accordance with the present invention greatly reduces the number of parts required to provide a flexible dental implant system, substantially reduces the cost of many of these components, and provides significant flexibility not heretofore seen in such systems and methods.

BRIEF DESCRIPTION OF THE DRAWINGS

FIGS. 1–16 depict a prosthodontic procedure employing the principles of the present invention.

FIGS. 28 and 29 depict alternative screws that may be employed to attach the temporary abutment of the present invention to an implant;

FIG. 30 is a front, elevational cut-away view depicting a another exemplary temporary abutment, implant member, and snap fit system;

FIG. 31 is a cutaway view taken along lines 31—31 in FIG. 30;

FIG. 32 is a front elevational view depicting an impression feather having a base portion that forms a part of the snap fit system shown in FIG. 31;

FIG. 33 is a bottom plan view of the impression coping shown in FIG. 32;

FIG. 34 is an elevational cut-away view depicting yet another exemplary temporary abutment and implant.

DETAILED DESCRIPTION

Referring initially to FIGS. 1–16, depicted therein is a prosthodontic procedure for fabricating and implanting a tooth prosthesis. This procedure employs a system for making impressions constructed in accordance with, and embodying, the principles of the present invention.

As an overview, the prosthodontic procedure shown in FIGS. 1–16 can be broken down into five distinct phases each comprising a number of steps:

PHASE 1: FIGS. 1–4 show what is referred to as stage one surgery in which an implant is placed into the jaw bone.

Figure 5:
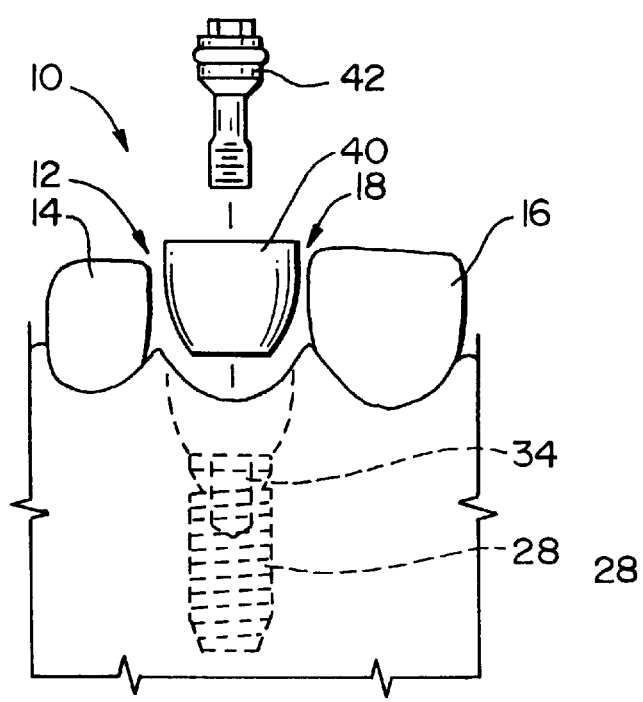
Figure 6:
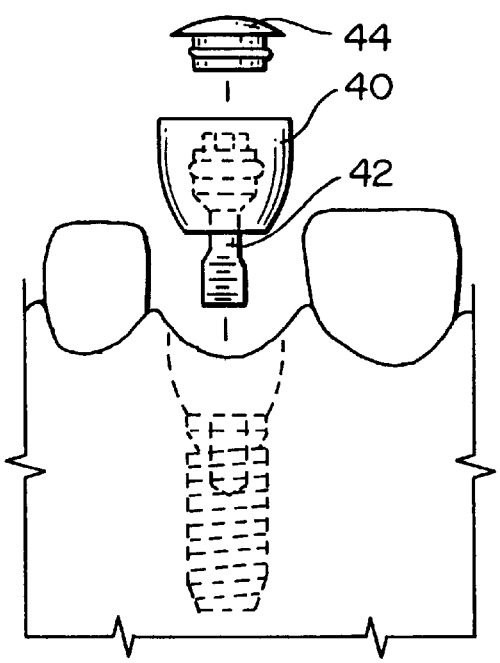
Figure 7:
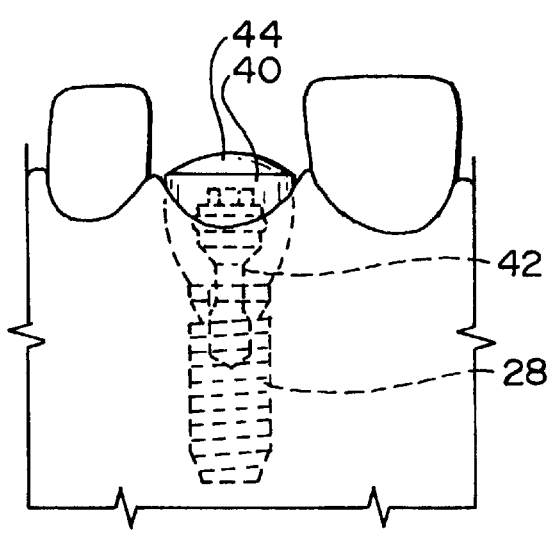

PHASE 2: FIGS. 5–7 depict what is referred to as stage two surgery in which a healing abutment is attached to the implant.

PHASE 3: FIGS. 8–11 depict the impression stage in which an impression is made of the patient's mouth.

PHASE 4: FIGS. 12–15 depict the restorative phase in which the impression is used to fabricate a prosthetic tooth.

Figure 16:
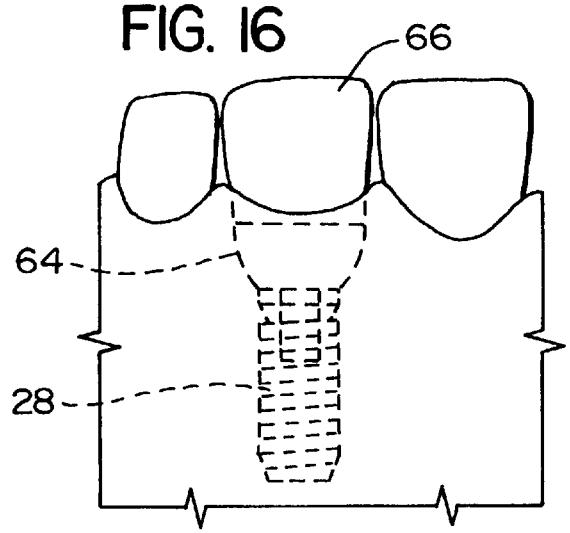

PHASE 5: FIG. 16 depicts the final stage in which the prosthetic tooth is mounted onto the implant.

To provide some perspective, initial reference is made to FIG. 5, which shows a portion of a patient's mouth 10 where a gap 12 exists between first and second adjacent teeth 14 and 16. Shown at 18 in FIG. 5 is the site at which the prosthetic tooth is to be located. FIG. 1 is a slightly enlarged cut-away view of the patient's mouth 10 at the gap 12.

Additionally, during the process depicted in FIGS. 1–16 the various steps will normally be performed by a periodontist or oral surgeon, a dentist, and laboratory technicians. In particular, a surgeon will normally perform the steps associated with Phases 1 and 2 described above, a dentist will perform the steps associated with Phases 3 and 5, and laboratory technicians will perform the steps associated with Phase 4.

During the first phase of the prosthodontic procedure, often referred to as stage one surgery, the surgeon makes an incision in the patient's gum 20 to expose the edentulous, or jaw, bone 22. The surgeon then drills a hole 24 in the jaw bone 22 (FIG. 1). The surgeon then taps the inner surface 26 of the jaw bone 22 surrounding the hole 24 such that this surface 26 is threaded (FIG. 2). A metallic fixture insert 28 having a threaded outer surface 30 matching the inner surface 26 is then threaded into the hole 24 in the bone 22 (FIG. 3).

The insert 28 also has a threaded inner surface 32 defining a screw chamber 34. After the insert 28 has been threaded into the jaw bone 22, a cover screw 36 is threaded into the screw chamber 34. The gum 20 is then sutured as shown at 38 such that the gum 20 covers the entire implant 28 and cover screw 36 (FIG. 4).

At this point, stage one surgery is complete and the patient enters an osseointegration period of approximately 3–6 months. The osseointegration period allows the jaw bone to integrate the implant 28. During the osseointegration period, primarily for cosmetic reasons the patient will usually wear what is referred to as a flipper (not shown) over the implant site 18.

After the implant 28 has been integrated into the jaw bone 22, the patient enters the second phase of the procedure, commonly referred to as phase two surgery, in which the surgeon attaches a temporary abutment 40 onto the insert 28. To accomplish this, the surgeon assembles an abutment screw 42 onto the temporary abutment 40 (FIGS. 5 and 6). The abutment screw 42 passes through the temporary abutment 40 and into the screw cavity 34 formed in the insert 28. The abutment screw 42 is then tightened to attach the temporary abutment 40 onto the insert 28 (FIG. 7). An abutment cap 44 is placed onto the temporary abutment 40 over the screw 42 (FIGS. 6 and 7). The gum tissue is then allowed 1–3 weeks to heal.

The temporary abutment 40 and abutment cap 44 are made with a low profile such that, when installed, they are approximately same level as the gum line. Accordingly, while the gum tissue is healing around the temporary abutment 40, a flipper may be worn over location 12 without interference by the temporary abutment 40 or abutment cap 44.

Figure 8:
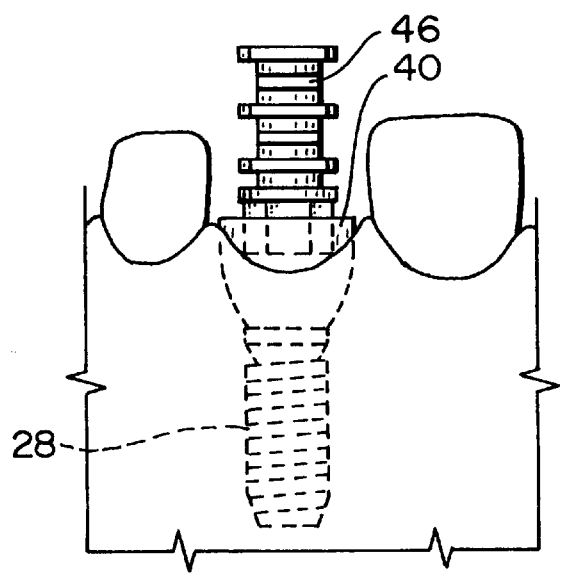
Figure 9:
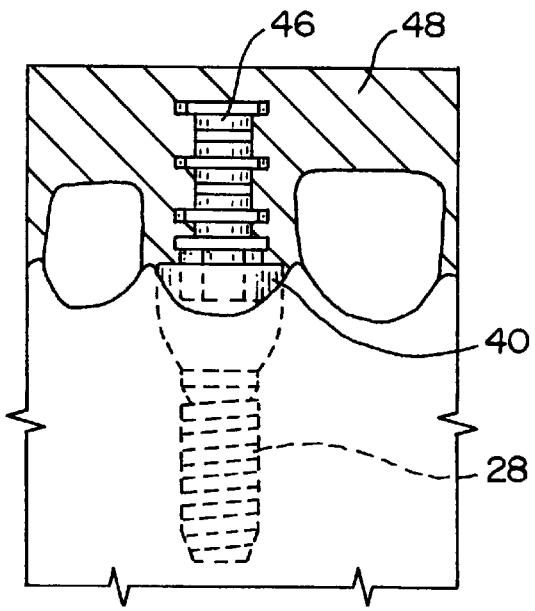

After the gum has healed from the affects of stage two surgery, the patient goes to the dentist responsible for the restorative work. The dentist will initially remove the cap 44 and attach what will be referred to herein as an impression feather 46 onto the temporary abutment 40 (FIG. 8). The dentist then positions an impression tray (not shown) over the impression feather 46 and inserts impression material 48 into the impression tray around the impression feather 46 (as well as the surrounding gum and teeth).

Figure 10:
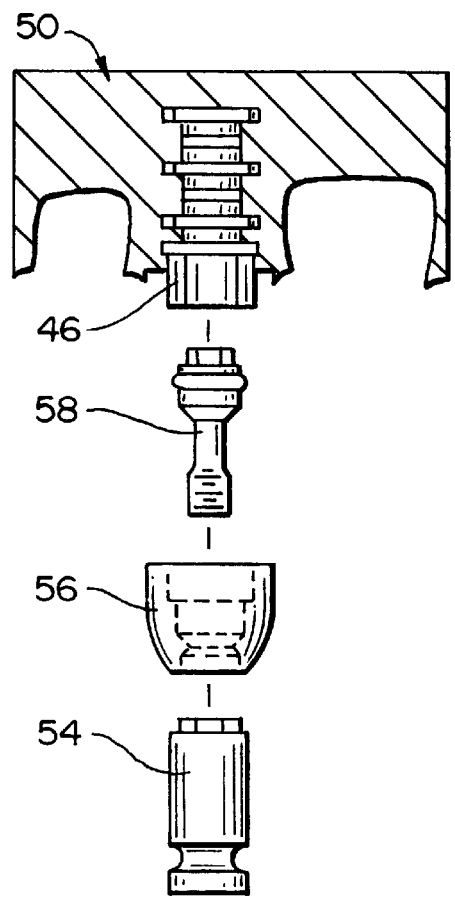

The impression material 48 solidifies to form an impression 50 comprising the solidified impression material 48 and the impression feather 46 (FIG. 10). The impression 50 is removed from the patient's mouth and sent to the laboratory for the restorative work.

Figure 11:
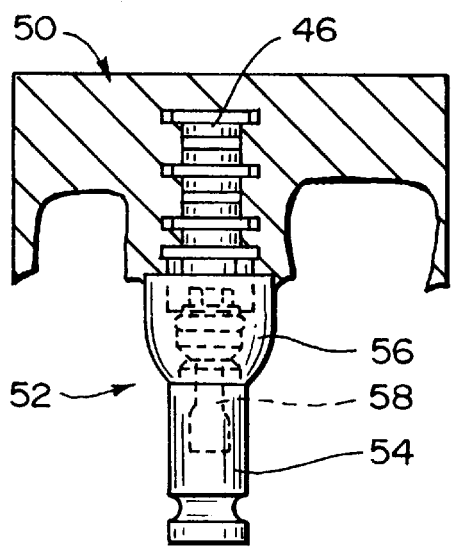

Upon receiving the impression 50 from the dentist, the laboratory technicians will form an analog assembly 52 comprising an implant analog 54, a temporary abutment 56 identical to the abutment 40 attached to the implant 28, and a screw 58 to hold the implant analog 54 and temporary abutment 56 together (FIGS. 10 and 11).

The temporary abutment 56 is then attached onto the impression feather 46 such that the implant analog 52 is spaced and extends from the impression feather 46 in the same manner as the implant 28 (FIG. 11).

Figure 12:
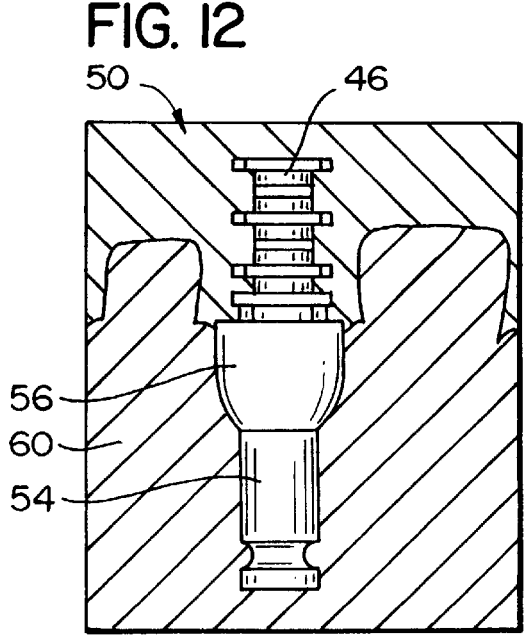
Figure 13:
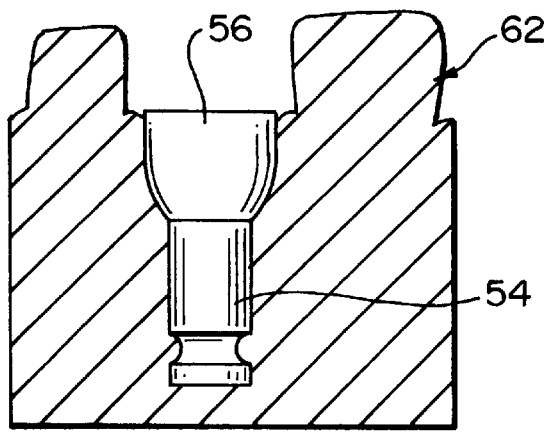

Model material 60 is then placed onto the impression 50 around the analog assembly 52 (FIG. 12). The model material 60 solidifies to form a model 62 and the impression 50, including the impression feather 46, is removed from the model 62. At this point, the temporary abutment 56 is still mounted on the implant analog 54 by the screw 58 (FIG. 13).

Figure 14:
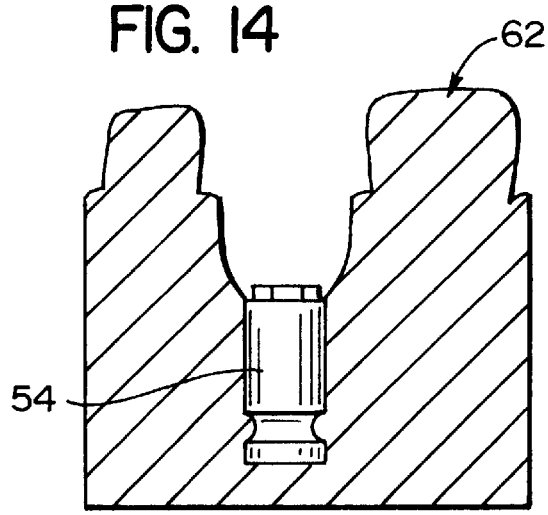

The next step is to remove the screw 58 and temporary abutment 56 from the model 62 (FIG. 14). The model now corresponds to the patient's mouth, with the implant analog 54 at a location corresponding to that of the implant 28 in the patient (FIG. 14).

Figure 15:
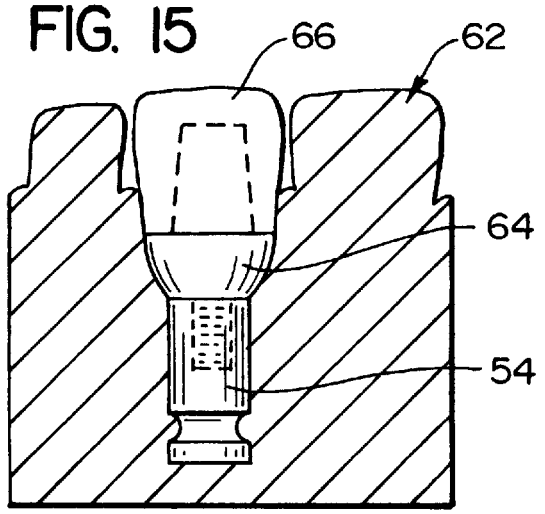

At this point, a permanent abutment 64 may be selected and attached to the implant analog 54 to allow the fabrication of a tooth prosthesis, or replacement tooth, 66 (FIG. 15).

Once the replacement tooth 66 has been fabricated, the patient goes back to the dentist where the temporary abutment 40 is removed and the permanent abutment 64 and replacement tooth 66 attached to the implant 28 (FIG. 16).

The prosthodontic procedure described above will vary depending upon such factors as the desires of the patient, the techniques employed by the surgeon and dentist, and the type of restorative work involved. Within this overall context, however, the systems and methods of the present invention provide a number of benefits.

For example, the systems and methods of the present invention greatly simplify the dentist's job during Phase 3 when the dentist makes the impression. The dentist need only remove the abutment cap and insert the impression feather before making the impression. After the impression is removed, the dentist simply replaces the abutment cap. The dentist need not remove and reinsert the healing abutment when making the impression.

Additionally, the style of permanent abutment may be selected in the laboratory during Phase 4 and need not be known at the time the impression is made. The present invention thus greatly simplifies the dentists job by reducing the number of implant parts that the dentist must keep in inventory and track for each patient.

Another important aspect of the present invention is that certain key parts may be made cheaply out of disposable plastic and not out of surgical grade metals. In particular, the temporary abutment, abutment cap, abutment screw, and impression feather may be made wholly or in part out of plastic. Making these parts out of plastic allows them to made cheaply enough to be disposable and obviates the need to sterilize them between each use.

Referring now to FIGS. 17–35, a number of components that may be used with the basic procedure described in relation to FIGS. 1–16, or minor variations thereof, will be described. The procedure depicted in FIGS. 1–16 may be performed with improved results over similar prior art methods without the exact components described in relation to FIGS. 17–35, but these components optimize the performance of this procedure.

Before describing the particulars of the components depicted in FIGS. 17–35, several important concepts should be explained. At the heart of the process depicted in FIGS. 1–16 are the temporary abutments 40 and 56. These abutments are intermediate members that transition between the implant 28 (or implant analog 46) and one or more other components the positions of which need to be fixed relative to the implant. The abutments 40 and 56 thus perform two basic functions: they engage the implant 28 and they form a snap fit that securely mounts another component relative to the implant (or the analog thereof).

The physical structure necessary to engage the implant is dependent upon the exact implant selected. Temporary abutments having structure necessary to engage three commercially available implants are depicted in FIGS. 19A–D, 28, and 29. Other structures may be similarly formed to engage other implants not discussed in this application. The formation of the appropriate structure for a given implant type can be easily implemented during the process of fabricating the mold used to manufacture a given temporary abutment. And typically, it will be necessary to manufacture and carry in inventory temporary abutments having structure adapted to engage any implant that is commercially available on a significant level.

The snap fit of the present invention can also be formed in one of a number of different ways. A first exemplary snap fit is embodied in the components shown in FIGS. 19A–D and 20, 22A–B, 26, 27, 28, and 29. A second exemplary snap fit system is embodied in the components shown in FIGS. 30–34.

The exact details of the snap fit are not critical to implement the principles of the present invention and other snap fit systems may be employed with similar effect. To function flexibly and reliably, the snap fit systems of the present invention have two characteristics: first, they are formed of projections and depressions that mate to positively hold one member onto another; and second they have a geometric shape that can be used to key one component relative to another. While both of these characteristics have advantages in the particular environment described, the present invention can be practiced with snap fit systems having either or neither of these characteristics and still obtain certain advantages over the prior art.

Once the details of the snap fit are determined, all components should be manufactured with the selected snap fit. Unlike the situation in which a number of different temporary abutments will normally be manufactured to match each style of commercially available implant, only one snap fit system needs to be and should be employed.

The various components used to implement the basic prosthodontic procedure described above with reference to FIGS. 1–16 will now be described. In the following discussion, the geometry of these components will first be described in detail, after which the function of the component geometry will be discussed.

Referring initially to FIGS. 19A–D, depicted therein at 110 is a temporary abutment identical to the abutments 40 and 56 described above. The temporary abutment 110 has a longitudinal axis A, an outer surface 112, and an inner surface 114 defining a centrally extending bore 116.

The outer surface 112 comprises an upper portion 118, a side portion 120, and a lower portion 122. The upper and lower surface portions 118 and 122 are flat and generally arcuate. The side surface portion 120 comprises a generally cylindrical upper area 124 adjacent to the upper surface portion 118 and curved lower area 126 adjacent to the lower surface portion 122. The lower area 126 is smoothly and continuously curved from the upper area 124 to the lower surface portion 122.

The inner surface 114 defines the shape of the central bore 116 such that the bore 116 comprises a lock portion 128, a screw receiving portion 130, and a hex receiving portion 132.

Figure 19A:
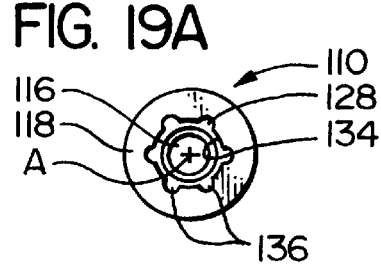
FIGS. 19A–D depict an exemplary temporary abutment as used in the procedure depicted in FIGS. 1–16.
Figure 19B:
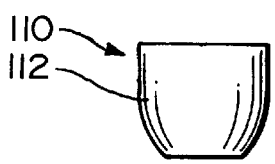

As perhaps best shown in FIG. 19A, the lock portion 128 of the central bore 116 has a shape that will be referred to herein as "coronal". In particular, the lock portion 128 is defined by a generally cylindrical first portion 134 of the inner surface 114 having a diameter d1. Vertical grooves 136 formed in the inner surface first portion 134 further define the shape of the lock portion 128.

Additionally, a locking groove 138 (FIG. 19D) is formed on the first portion 134 of the inner surface 114. The vertical grooves 136 extend through the inner surface first portion 134 and the locking groove 138 such that the inner surface portion 134 and the groove 138 are discontinuous.

The screw receiving portion 130 of the central bore 116 is defined by a generally cylindrical second portion 140 of the inner surface 114 having a diameter d2. This diameter d2 is less than the diameter d1 of the inner surface first portion 134. A rounded, annular, horizontal retaining projection 142 extends from the inner surface second portion 140 adjacent to the central bore lock portion 128.

The hex portion 132 of the central bore is defined by a six-sided hex portion 144 of the inner surface 114. This shape is perhaps best shown in FIG. 19C.

First and second conical portions 146 and 148 of the inner surface 114 are formed on a triangular, annular, horizontal projection 150 arranged between the inner surface second portion 140 and the inner surface hex portion 144. The conical surface portions 146 and 148 meet at an annular transition ridge 152. The conical surface portions 146 and 148 and transition ridge 152 define a transition portion 154 of the central bore 116.

Figure 18:
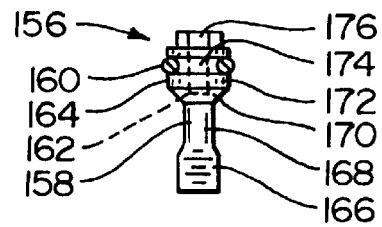
FIG. 18 depicts an exemplary abutment screw assembly as used in the procedure depicted in FIGS. 1–16.

Referring now to FIG. 18, depicted therein at 156 is an abutment screw assembly identical to the abutment screw assemblies 42 and 48 described above. The abutment screw assembly 156 comprises a screw body 158 and an O-ring 160.

The screw body 158 has a threaded internal surface 162 and an external surface 164. The external surface 164 comprises, from bottom to top in FIG. 18, a threaded portion 166, a shaft portion 168, a conical portion 170, an increased diameter portion 172, an O-ring groove 174, and a hex body 176.

To obtain the assembly 156, the O-ring 160 is seated in the O-ring groove 174. When so seated, incidental movement between the screw body 158 and the O-ring 160 is prevented.

Figure 21:
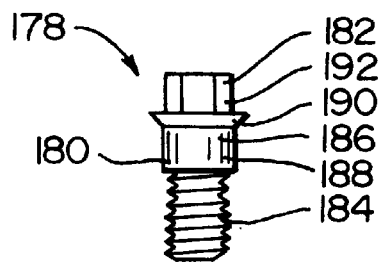
FIG. 21 depicts an alternative abutment screw assembly that may be used in many situations in place of the abutment screw assembly shown in FIG. 18.

Referring now to FIG. 21, depicted therein is an abutment screw assembly 178 used in a manner similar to the abutment screw assemblies 42 and 48 described above.

The abutment screw assembly 178 comprises a screw body 180 and a seating cap 182. The screw body 180 is a simple cylinder with an externally threaded outer surface 184. The seating cap 182 has an outer surface 186 having a cylindrical portion 188, a conical portion 190, and a hex portion 192. The seating cap 182 is rigidly connected to the screw body 180 such that axial rotation of the cap 182 is transmitted to the body 180.

Referring now to FIGS. 28 and 29, these figures illustrate how the abutment screw assemblies 156 and 178 engage the temporary abutment 110. In both cases, the annular retaining projection 142 on the interior surface 114 of the abutment 110 engages a portion of the screw assembly such that the screw assembly is captured within the central bore 116.

More particularly, as shown in FIG. 28 the flexible O-ring 160 has a slightly larger diameter than the annular retaining projection 142. The screw assembly 156 may be inserted into the central bore 116 such that the O-ring 160 is within the screw receiving portion 130 of the central bore 116, however, because the O-ring 160 is compressible and deflects slightly to allow it to enter the screw receiving portion 130. Once the O-ring is within the bore portion 130, the O-ring 160 will engage the retaining projection 142 to prevent inadvertent removal of the screw assembly 156. But deliberate application of force in a direction shown by arrow C will cause the O-ring 160 to compress and allow the screw assembly 156 to be removed from the central bore 116.

Similarly, as shown in FIG. 29 the conical surface 190 of the screw assembly 178 has a slightly larger diameter than the annular retaining projection 142. By manufacturing at least the seating cap 182 of the screw assembly 178 out of plastic, the parts may be fabricated such that the conical surface 190 will pass by the retaining projection 142 such that the hex body 192 is within the screw receiving portion 130 of the central bore 116. Once the conical surface is within the bore portion 130, the seating cap 182 will engage the retaining projection 142 to prevent inadvertent removal of the screw assembly 178. But deliberate application of force in a direction shown by arrow C will allow the screw assembly 156 to be removed from the central bore 116 if desired.

Additionally, in each of the situations shown in FIGS. 28 and 29, some movement between the screw assemblies 156 and 178 and the abutment 110 along the abutment axis A is allowed. As will be explained in further detail below, this allows the abutment to be lifted slightly and rotated relative to the insert even after the position of the screw assembly is fixed.

Figure 17:
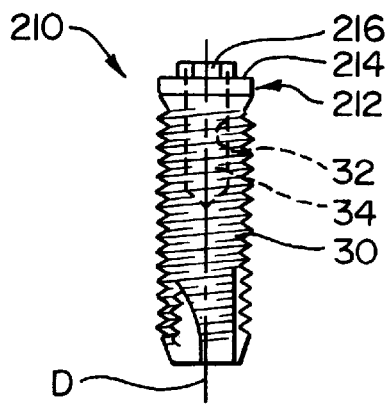
FIG. 17 depicts an exemplary implant used in the procedure depicted in FIGS. 1–16.

Referring now to FIG. 17, depicted therein is an implant 210 identical to the implant 28 described above. The implant 210 is conventional and will be described herein only to the extent necessary for a complete understanding of the present invention.

The implant 210 has, in addition to the threaded external surface 30, threaded internal surface 32, and screw cavity 34 briefly described above, an upper shoulder 212, upper surface 214, and hex body 216. The upper shoulder 212 is generally cylindrical. The upper surface 214 is flat, disc-shaped, and is bounded at its outer periphery by the shoulder 212. The hex body 216 extends from the upper surface 70. The screw cavity 34 passes through the upper surface 212 and the hex body 214. The entire implant 28 is generally symmetrical about its longitudinal axis D, with the external surface 30, internal surface 32, screw cavity 34, upper shoulder 212, upper surface 214, and hex body 216 all being coaxially aligned with the longitudinal axis D.

Figure 20:
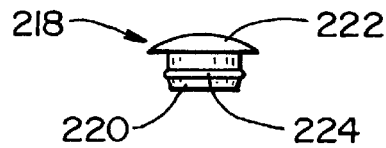
FIG. 20 depicts an exemplary abutment cap used in the procedure depicted in FIGS. 1–16.

Referring now to FIG. 20, depicted therein is an abutment cap 218 identical to the abutment cap 44 described above. The abutment cap 218 comprises a cylindrical base portion 220, a dome-shaped cover portion 222, and a locking ring 224.

Figure 22A:
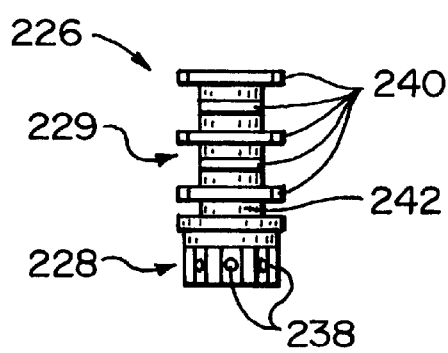
FIGS. 22A–B depict an exemplary impression feather used in the procedure depicted in FIGS. 1–16.
Figure 22B:
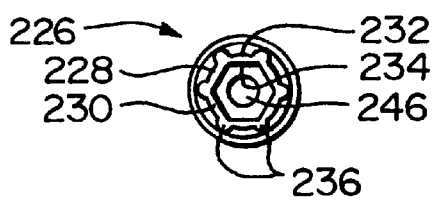

FIGS. 22A and 22B illustrate an impression feather 226 identical to the impression feather 46 described above. The feather 226 comprises a base portion 228 and an upper portion 229. The overall shape of the base portion 228 is perhaps best shown in FIG. 22B and is sized and configured to match the dimensions of the lock portion 128 of the central bore 114 of the temporary abutment 110.

In particular, the base portion 128 comprises a wall 230 having a cylindrical outer surface 232 and a hex-shaped inner surface 234. Projecting at intervals from the from the outer surface 232 are vertical alignment projections 236. The base portion outer surface 232 is dimensioned to fit snugly within the cylindrical inner portion 134 of the abutment inner wall 114. The alignment projections 236 are similarly dimensioned to fit snugly within the alignment grooves 136 formed in the abutment inner wall 114. The base portion 128 of the impression feather 226 may thus be received within the lock portion 128 of the abutment central bore 116 in a manner prevents relative axial rotation between the feather 226 and the abutment 110.

Additionally, locking projections 238 extend from the cylindrical outer surface 230 of the base wall 228.

The upper portion 229 of the impression feather 226 comprises a series of horizontal flanges 240 that extend from a central post 242. The flanges 240 are offset from the flanges above and below by 90 degrees. The purpose of the flanges 240 is to create a secure interconnection between the impression feather 226 and the impression in which it is captured.

With an understanding of the shape of the foregoing components 110, 156, 178, 210, 218, and 226, certain steps in the prosthodontic procedure illustrated in FIGS. 1–16 will be now described in further detail.

Referring initially to the step depicted in FIG. 6, in that step the abutment screw 42 is captured within the temporary abutment 40 as described above and may thus be transported to the patient's mouth as an assembly. This lessens the likelihood that the surgeon will drop or otherwise mishandle the components used during stage two surgery.

Between FIGS. 6 and 7, the abutment cap 44 has been placed onto the temporary abutment 40. The cap 44 is manufactured such that it engages the temporary abutment 40 with a simple snap fit. More specifically, the locking ring 224 formed on the cap 44 is sized, dimensioned, and spaced from the cover portion 222 thereof such that the ring 224 engages the locking groove 138 formed on the inner surface 114 of the abutment 40. So engaged, the cover portion 222 of the cap 44 nests snugly against the upper surface 118 of the abutment 40 to prevent material from entering the center bore 116.

Between the steps depicted in FIGS. 7 and 8, the abutment cap 44 is removed from the temporary abutment 40. To facilitate this removal, a notch 242 (FIG. 19B) is formed on the abutment 110. A dental pick may be inserted into this notch under the cap cover portion 222 to pop the cap 44 off of the abutment 40.

Prior to the step shown in FIG. 8, the impression feather 46 was attached to the temporary abutment 40. This attachment is made by a snap fit similar to that employed to attach the cap 44 onto the abutment 40. In particular, the locking projections 238 formed on the base 228 of the impression feather 46 engage the locking groove 138 formed on the inner surface 114 of the abutment 40. This engagement prevents inadvertent removal of the impression feather 46 from the abutment 40 but may easily be overcome by the application of deliberate force on the impression feather 46 away from the abutment 40.

An identical attachment is formed between the impression feather 46 in the impression 50 and the second temporary abutment 56 as shown in FIGS. 10 and 11.

Many of the components described above may be made out of any material that is biologically inert and strong enough to withstand the loads encountered during insertion and while being worn in the patient's mouth. Certainly any surgical grade metal such as titanium would work satisfactorily, although the primary benefits of the present invention are obtained by manufacturing the at least portions of these components out of dental grade plastic.

In particular, the temporary abutment 110, seating cap 182, abutment cap 224, and impression feather 226 are all preferably fabricated out of plastic such as an acetyl copolymer. In any situation where a snap fit is employed to attach two components together, at least one, and preferably both, of these components must be manufactured out of plastic to allow the deflection necessary to achieve the snap fit.

Referring now to FIGS. 23–27, depicted therein are certain additional components that may be employed using the systems and components of the present invention. It should be noted that these additional components will normally be used during variations of the basic procedure depicted in FIGS. 1–16 as fits a particular circumstance.

Figure 24:
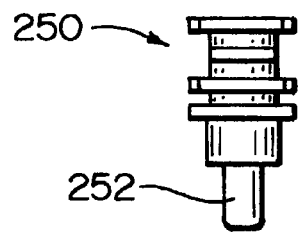
FIG. 24 depicts a surgical impression coping that may be used to take an impression during stage one surgery.
Figure 26:
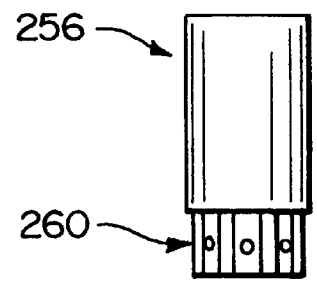
FIGS. 26 and 27 depict members that may be used during the restoration process for replacing a tooth with a temporary tooth to allow for further maturation of the implant in the bone.
Figure 23:
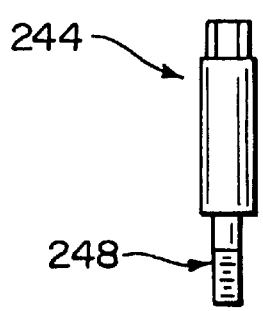
FIG. 23 depicts an exemplary pick up post that may be used to take an impression.
Figure 27:
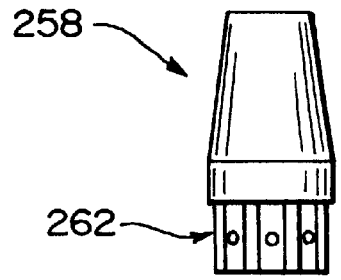

FIG. 23 depicts a pick up post 244 that passes through a central bore 246 formed in the impression feather 226 or in one of the members depicted in FIGS. 24, 26, or 27. A threaded end 248 of the post 244 allows the post 244 to fix the position the member through which it passes relative to an implant.

FIG. 24 depicts a surgical impression feather 250 that may be used during phase one surgery to obtain an impression indicating the location of the implant. A lower post 252 of the surgical impression feather 250 enters the screw chamber 34 defined by the implant to form a friction fit that holds the feather 250 in place while the impression is being taken. The post 252 is not threaded, however, and may be withdrawn when the impression is removed.

Figure 25:
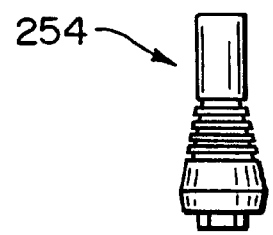
FIG. 25 depicts a temporary cylinder that may be used to take an impression.

FIG. 25 depicts a temporary cylinder 254 adapted to be attached to the temporary abutment 110 by the pick-up post 244. The bottom end thereof has a corona type fastener to key the cylinder 256 relative to the temporary abutment 110.

FIGS. 26 and 27 depict a cylinder 256 and a preped abutment 258, respectively. These members 256 and 258 may be attached to the temporary abutment 110 and implant 210 and preped like a tooth to support a temporary or permanent restoration. These members 256 and 258 have bases 260 and 262 that allow them be snap fit onto a temporary abutment such as the temporary abutment 110.

Figure 35:
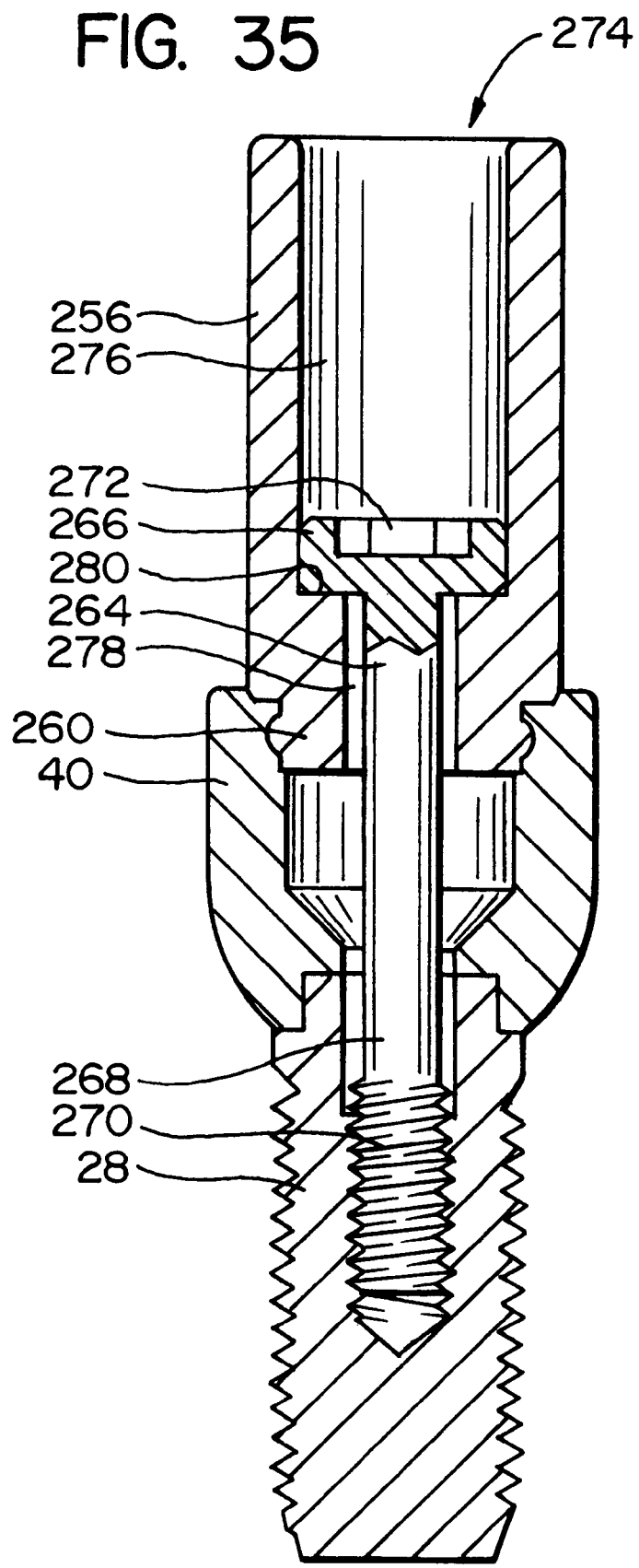
FIG. 35 is a front, elevational, cut-away view depicting a screw employed to mount the temporary cylinder of FIG. 26 onto a temporary abutment member.

FIG. 35 depicts the cylinder 256 attached to the abutment 40 and implant 28 by a screw 264. The base 260 of the cylinder 256 engages and forms a snap-fit with the abutment 40. The screw 264 has a head portion 266, a shaft portion 268, and a threaded portion 270. A hex recess 272 is formed in the head portion 270. The cylinder 256 defines a central bore 274 having a first, larger diameter portion 276 and a second, smaller diameter portion 278. A shoulder surface 280 is formed at the juncture of the bore portions 274 and 276.

The shaft portion 268 of the screw spaces the treaded portion 270 from the head portion 266 such that, when the threaded portion 270 is rotated onto the threaded surface 32 of the implant 28, the head portion 266 acts on the shoulder surface 280 to hold the cylinder 256 onto the abutment 40 and the abutment 40 onto the implant 28. The base 260 thus keys the cylinder 256 onto the abutment 40, and the screw 264 holds the assembly of the cylinder 256, abutment 40, and implant 28 together. The cylinder 256 can thus support, on a temporary basis, a temporary or permanent restoration.

Referring now to FIG. 30, depicted therein is a prosthodontic assembly 310 comprising a temporary abutment 312, implant 314, and screw 316. The temporary abutment 312 has a longitudinal axis A, an outer surface 318, and an inner surface 320 defining a centrally extending bore 322. The implant 314 has an external surface 324 having a threaded portion 326 and an internal surface 328 having a threaded portion 330. The screw 316 has a head portion 332 and a shaft portion 334. A threaded surface 336 is formed on the shaft portion 334.

In general, the screw 316 attaches the temporary abutment 312 to the implant 314. The specific structure that allows this attachment will be described in further detail below.

In general, the screw 316 passes through the central bore 322 such that the threaded surface 336 on the screw engages the threaded portion 330 of the internal surface 328 of the implant 314.

The outer surface 318 differs from the outer surface 312 of the temporary abutment 110 described above in that it is adapted to mate with the implant 314. In particular, the exterior surface 324 of the implant 314 has a conical portion 338 that forms a shoulder of the implant 314. The interior surface 328 of the implant 314 defines, in addition to the threaded portion 330 described above, a hex portion 340. Referring to FIG. 31, it can be seen that the hex portion 340 defines a hex chamber. To allow the temporary abutment 312 to securely engage the implant 314, a frustoconical surface 342 and hexagonal projection 344 are formed thereon. The abutment conical surface 342 is angled with respect to the longitudinal axis A to abut the frustoconical surface 338 formed on the implant 314. Similarly, the hexagonal projection 344 is sized and dimensioned to be snugly received within the chamber defined by the hexagonal surface 340 on the implant member 314. Thus, when the temporary abutment 312 is attached to the implant 314, the conical surfaces 338 and 342 abut each other and the hexagonal projection 344 on the abutment 110 is received within the hexagonal cavity defined by the hexagonal surface 340 on the implant 314.

The central bore 322 comprises a lock portion 346 and a screw receiving portion 348. The lock portion 346 is similar in operation to the lock portion 128 of the central bore 116 described above.

The lock portion 346 is defined by a first portion 348 of the interior wall 320. This wall portion 348 is generally hexagonal in shape. In particular, this wall portion 348 comprises six identical wall segments 350 each having an elliptical recess 352 formed therein.

Referring now for a moment to FIGS. 32 and 33, depicted therein is an impression coping 354 adapted to mate with the temporary abutment 312. The impression coping 354 is in most respects the same as the impression coping 226 described above. The primary difference between these is that a base portion 356 of the coping 354 is adapted to mate with the temporary abutment 110.

In particular, the base portion 356 has a hexagonal body 358 having six identical surfaces 360, with a projection 362 formed on each of the surfaces 360. The hex member 358 is sized and dimensioned to be snugly received within the locked portion 346 of the central bore 322, with the projections 362 being received within the recesses 352. The recesses 362 engage the projections 362 to form a snap pit that locks the impression coping 354 onto the temporary abutment 312 as described above. The locking system formed by the base portion 356 of the impression coping 354 and the first portion 346 of the central bore 322 maintains the impression coping in an appropriate relationship to the temporary abutment 312 during the process of taking the impression. But the impression coping 354 can be removed by the application of deliberate manual force on the impression coping 354 away from the temporary abutment 312.

It should be recognized that the base portion 356 of the impression coping 354 may be substituted on any of the components described above that are intended to be mounted on to the temporary abutment 110. The impression coping 354 is simply exemplary of these other components.

Referring now to FIG. 30, it can be seen that the central bore 322 further comprises a second, head receiving portion 364. This head receiving portion 364 is defined by a cylindrical wall 366 and a frustoconical wall 368. The head portion 332 of the screw 316 has a frustoconical wall 370 that is arranged at the same angle as the wall 368. Accordingly, as the screw 316 is axially rotated, its threaded surface 336 engages the threaded portion 330 of the implant 314 to pull the conical surface 370 on the head portion 332 against the conical surface 368 defining the head receiving portion 364.

Referring now to FIG. 34, depicted at 410 therein is yet another exemplary implant assembly constructed in accordance with, and embodying, the principles of the present invention. This assembly 410 comprises yet another exemplary temporary abutment 412 that is attached to an implant 414. The implant 414 is a special type of implant referred to as a Morris taper. The temporary abutment 412 has been modified to the Morris taper style implant 414.

The implant 414 has an exterior surface 416 and an interior surface 418. The exterior surface is adapted to be threaded into a patient's bone and be osseointegrated therewith. An upper portion 420 of the exterior surface 416 is formed in a downwardly tapering frustoconical shape. The inner surface 418 has an upwardly tapering frustoconical surface 422 that extends at an angle of approximately 6 degrees relative to the longitudinal axis of the implant 414. These two surfaces 420 and 422 meet at an annular uppermost portion 424 of the implant 414.

The inner surface 418 of the implant 414 thus defines a frustoconical region 426 above a threaded region 428 defined by a threaded surface 430. This arrangement allows the temporary abutment 412 to be directly threaded onto the implant 414, obviating the need for a separate screw.

The temporary abutment 412 thus does not have a central bore extending all the way therethrough, instead having an upper cavity 432 defined by an inner wall 434. The inner wall 434 has an upper portion 436 comprising six surfaces 438 each having an elliptical or ovoid depression 440 formed therein. Inner wall 434 also has a cylindrical portion 442. The upper cavity 432 operates in the same basic manner as the first and second portions of the central bore 322 described above to allow components having a base portion such as the base portion 356 of the impression coping 354 described above to be attached to the temporary abutment 412.

Formed on a lower portion of the temporary abutment 110 is an inwardly facing frustoconical surface 444 and an outwardly facing frustoconical surface 446. The surfaces 444 and 446 are sized and dimensioned to match the surfaces 420 and 418, respectively, formed on the implant 414. The abutment outer surface 446 further comprises a threaded portion 450 below the frustoconical portion 448. The surface portions 446, 448, and 450 are arranged and dimensioned relative to each other to allow the temporary abutment 410 to be threaded onto the implant 414 as follows. The threaded surface portion 450 engages the threaded inner surface portion 430 of the implant 414 such that, when the abutment 412 is rotate about its axis, these threaded surfaces engage to displace the temporary abutment 412 towards the implant 414. At some point, the surfaces 446 and 448 will engage the surfaces 420 and 418 to snugly attach the temporary abutment 4122 onto the implant 414. The abutment can then be used in the same basic manner as the temporary abutments of the present invention as described above.

Figure 19C:
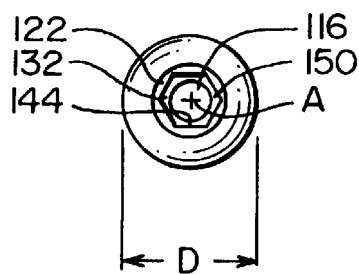
Figure 19D:
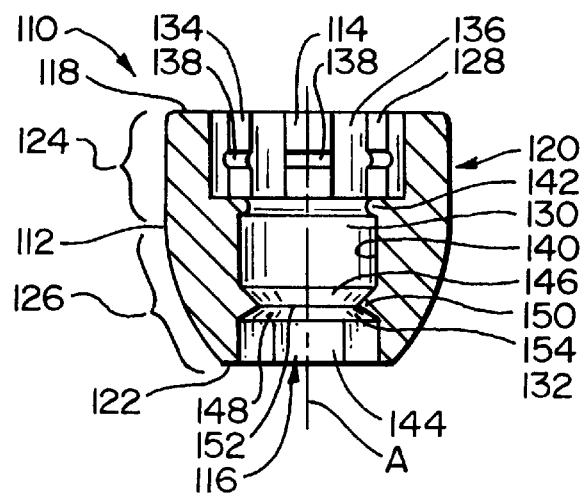

Another aspect of the present invention not readily apparent from the drawings is the relative size of the various components shown and described herein. For example, the temporary abutments may be sold with different external diameters D (FIG. 19C). An appropriate abutment diameter is then selected for a particular situation. Other components, such as the cap 218 and impression coping 226, need not be provided in different sizes to match the different diameters of the temporary abutment. Thus, once the external diameter D is selected, no other size choices need be made in implement the procedure of the present invention. This allows, for example, only one type of cap 218 need be manufactured and kept in inventory.

From the foregoing, it should be clear that the invention may be embodied in other specific forms without departing from the spirit or essential characteristics thereof. The present embodiments are therefore to be considered in all respects as illustrative and not restrictive.

I claim:

1. A prosthodontic procedure for forming a dental impression indicating a location of an implant member comprising the steps of:

placing the implant member into a patient's jaw bone;

providing a first temporary abutment member having an inner wall defining a bore;

attaching the first temporary abutment member to the implant member;

providing a prosthodontic impression member having a base portion and an impression portion;

forming a recess on one of the inner wall of the first temporary abutment member and the base portion of the prosthodontic impression member;

forming a projection on the other of the inner wall of the first temporary abutment member and the base portion of the prosthodontic impression member;

displacing the prosthodontic impression member towards the first temporary abutment member until the projection engages the recess to form a snap fit that prevents inadvertent removal of the prosthodontic impression member but which allows the prosthodontic impression member to be removed by application of deliberate, manual force thereon;

embedding the impression portion of the prosthodontic impression member in impression material;

allowing the impression material to harden; and applying deliberate, manual force to the hardened impression material to displace both the hardened impression material and the prosthodontic impression member embedded therein away from the first temporary abutment member.

2. A prosthodontic procedure as recited in claim 1, further comprising the step of forming one of the first temporary abutment member and the prosthetic impression member out of plastic.

3. A prosthodontic procedure as recited in claim 2, in which both the first temporary abutment member and the prosthetic impression member are formed out of plastic.

4. A prosthodontic procedure as recited in claim 1, further comprising the steps of:

fabricating a prosthetic tooth using the hardened impression member and the prosthodontic impression member;

mounting the prosthetic tooth onto the implant.

5. A prosthodontic assembly for forming of an impression indicating a location of an implant member to allow fabrication of a prosthetic tooth, the prosthodontic assembly comprising:

an abutment member having an inner surface defining a bore having a first bore portion;

a screw member that extends through the bore in the abutment member and into the implant member to attach the abutment member to the implant member;

an impression member having a base portion adapted to mate with the first bore portion, where the impression member is in a desired position relative to the first prosthodontic member when the base portion mates with the first bore portion;

attachment means integrally formed on both the abutment member and the impression member for attaching the impression member onto abutment member in the desired position, where the impression member is attached to the abutment member in a manner that resists inadvertent removal of the impression member from the abutment member but allows removal of the impression member from the abutment member by application of deliberate, manual force on the impression member in a direction away from the abutment member.

6. A prosthodontic assembly as recited in claim 5, in which the attachment means comprises a projection formed on one of the inner surface of the abutment member and the base portion of the impression member and a recess formed on the other of the inner surface of the abutment member and the base portion of the impression member, the projection being sized, dimensioned, and located relative to the recess to enter and engage the recess when the impression member is in the desired position.

7. A prosthodontic assembly as recited in claim 6, in which at least one of the abutment and impression members is made of plastic.

8. A prosthodontic assembly as recited in claim 7, in which both the abutment and impression members are made of plastic.

9. A prosthodontic assembly as recited in claim 5, in which the inner surface of the abutment member further defines a second bore portion of the bore for receiving the screw member in a manner that allows the screw member to rotate relative to the abutment member until the screw member engages the inner surface to securely hold the abutment member against the implant member.

10. A prosthodontic assembly as recited in claim 9, in which the inner surface of the abutment member further defines a third bore portion of the bore adapted to receive a portion of the implant member in a manner that prevents rotation of the abutment member relative to the implant member when the abutment member is attached to the implant member.

11. A prosthodontic assembly as recited in claim 5, further comprising an abutment cap that temporarily covers the bore in the abutment member.

12. A prosthodontic procedure comprising the steps of:
  osseointegrating a first implant member at a desired location;
  attaching a first temporary abutment member to the first implant member;
  attaching an abutment cap member onto the first temporary abutment member;
  allowing gingival tissue around the first temporary abutment member to heal;
  removing the abutment cap member from the first temporary abutment member;
  attaching an impression member onto the first temporary abutment member;
  applying impression material to the impression member;
  allowing the impression material to solidify to form an impression in which the impression member is embedded;
  removing the impression member from the first temporary abutment member with the impression member still embedded in the impression;
  attaching a second implant member onto a second temporary abutment member
  attaching the second temporary abutment member to the impression member embedded in the impression;
  applying model material to the second temporary abutment member and second implant member;
  allowing the model material to solidify to form a model in which the second implant member is embedded;
  removing the second temporary abutment member from the impression member;
  removing the second temporary abutment member from the second implant member;
  attaching a permanent abutment member to the second implant member;
  forming a prosthetic member on the permanent abutment member;
  removing the first temporary abutment member from the first implant member; and
  attaching the permanent abutment member and prosthetic member to the first implant member.

13. A procedure as recited in claim 12, in which the step of attaching the abutment cap member onto the first temporary abutment member comprises the steps of:
  forming a projection on one of an inner surface of the first temporary abutment member and a base portion of the abutment cap member; and
  forming a recess on the other of the inner surface of the first temporary abutment member and the base portion of the abutment cap member; wherein
  the projection is sized, dimensioned, and located relative to the recess to enter and engage the recess when the abutment cap member is attached to the first temporary abutment member.

14. A procedure as recited in claim 12, in which the step of removing the abutment cap member from the first temporary abutment member comprises the step of applying deliberate manual force to the abutment cap member in a direction away from the first temporary abutment member.

15. A procedure as recited in claim 12, in which the step of attaching the impression member onto the first temporary abutment member comprises the steps of:
  forming a projection on one of an inner surface of the first temporary abutment member and a base portion of the impression member; and
  forming a recess on the other of the inner surface of the first temporary abutment member and the base portion of the impression member; wherein
  the projection is sized, dimensioned, and located relative to the recess to enter and engage the recess when the impression member is attached to the first temporary abutment member.

16. A procedure as recited in claim 12, in which the step of removing the impression member from the first temporary abutment member comprises the step of applying deliberate manual force to the impression in a direction away from the first temporary abutment member.

17. A procedure as recited in claim 12, in which the step of attaching the second temporary abutment member onto the impression member comprises the steps of:
  forming a projection on one of a base portion of the impression member and an inner surface of the second temporary abutment member; and
  forming a recess on the other of the base portion of the impression member and the inner surface of the second temporary abutment member; wherein
  the projection is sized, dimensioned, and located relative to the recess to enter and engage the recess when the second temporary abutment member is attached to the impression member.

18. A procedure as recited in claim 12, in which the step of removing the second temporary abutment member from the impression member comprises the step of applying deliberate manual force to the model in a direction away from the impression member.

19. A procedure as recited in claim 12, in which the step of attaching the first temporary abutment member onto the implant member comprises the steps of:
  forming a bore in the first temporary abutment member defined by an inner wall thereof;
  forming a threaded chamber in the implant member;
  providing a screw member having a threaded portion adapted to engage the threaded chamber in the implant member and an increased diameter portion;

passing the threaded portion of the screw member through the bore in the first temporary abutment member; and rotating the screw member such that the threaded portion thereof engages the threaded cavity in the implant member, thereby displacing the screw member until the increased diameter portion thereof engages the inner wall of the first temporary abutment member.

20. A procedure as recited in claim 19, in which the step of attaching the first temporary abutment member onto the implant member comprises the steps of:

forming a body portion on the implant member;

forming the bore in the first temporary abutment member such that the bore contains a receiving portion adapted to receive the body portion on the implant member; wherein the body portion of the implant member engages a portion of the inner wall of the first temporary abutment member that defines the receiving portion of the bore to prevent rotation of the first temporary abutment member relative to the implant member.

21. A method as recited in claim 12, in which the at least one of the first temporary abutment member, abutment cap, impression member, second temporary abutment member is made of plastic.

22. A prosthodontic procedure comprising the steps of:

placing an implant member into a patient's jaw bone;

providing a first temporary abutment member having a bore defined by an inner wall of the first temporary abutment member;

attaching the first temporary abutment member to the implant member;

providing a impression member having a base portion and a flanged portion;

forming a recess on one of the abutment member inner wall and the base portion of the impression member;

forming a projection on the other of the abutment member inner wall and the base portion of the impression member; and displacing the impression member towards the first temporary abutment member until the projection engages the recess to form a snap fit that prevents inadvertent removal of the impression member but which allows the impression member to be removed by application of deliberate, manual force thereon;

making an impression of the patient's mouth such that the flanged portion of the impression member is embedded in the impression;

fabricating a prosthetic tooth by making a model from the impression and the impression member;

mounting the prosthetic tooth onto the implant.

23. A prosthodontic procedure for transferring a location of an implant member implanted in a patient's mouth to a model of the patient's mouth, comprising the steps of:

providing a first temporary abutment member having a bore defined by an inner wall of the first temporary abutment member;

displacing the first temporary abutment member such that it engages the implant member;

fastening the first temporary abutment member to the implant member by passing a fastener through the bore in the first temporary abutment member and into a threaded cavity in the implant member;

providing a prosthodontic member having a base portion;

forming a recess on one of the abutment member inner wall and the base portion of the prosthodontic member;

forming a projection on the other of the abutment member inner wall and the base portion of the prosthodontic member;

displacing the prosthodontic member towards the first temporary abutment member until the projection engages the recess to form a snap fit that prevents inadvertent removal of the prosthodontic member but which allows the prosthodontic member to be removed by application of deliberate force thereon;

forming an impression of the patients mouth such that the prosthodontic member is embedded in the impression;

applying deliberate force to the impression such that the projection disengages from the recess, thereby allowing the impression and the prosthodontic member embedded therein to be removed from the patient's mouth;

providing a second temporary abutment member;

attaching the second temporary abutment member to the prosthodontic member embedded in the impression;

providing an analog of the implant member;

attaching the analog of the implant member to the second temporary abutment member to form an impression assembly; and forming the model of the patient's mouth from the impression assembly.

24. A prosthodontic procedure as recited in claim 23, further comprising the step of forming one of the first temporary abutment member and the prosthetic member out of plastic.

25. A prosthodontic procedure as recited in claim 24, in which both the first temporary abutment member and the prosthetic member are formed out of plastic.

26. A prosthodontic procedure as recited in claim 25, in which the prosthodontic member is an impression member.

27. A prosthodontic procedure as recited in claim 23, in which the prosthodontic member is an impression member, the procedure further comprising the steps of:

fabricating a prosthetic tooth using the model;

mounting the prosthetic tooth onto the implant.

28. A prosthodontic assembly comprising: an implant member implanted into a patient's jaw bone;

a first prosthodontic member having an inner surface defining a bore having first and second bore portions, where the first bore portion is adapted to mate with a portion of the implant member;

a second prosthodontic member having a base portion adapted to mate with the second bore portion, where the second prosthodontic member is in a desired position relative to the first prosthodontic member when the base portion mates with the second bore portion;

a fastener extending through the bore and into a threaded cavity in the implant member to fix the first prosthodontic member relative to the implant member; and attachment means comprising a projection and a recess for attaching the second prosthodontic member onto the first prosthodontic member in the desired position, where the projection engages the recess such that the second prosthodontic member is attached to the first prosthodontic member in a manner that resists inadvertent removal of the second prosthodontic member from the first prosthodontic member but allows removal of the second prosthodontic member from the first prosthodontic member by application of deliberate, manual force on the second prosthodontic member in a direction away from the first prosthodontic member.

29. A prosthodontic assembly as recited in claim 28, in which the projection is formed on one of the inner surface of the first prosthodontic member and the base portion of the second prosthodontic member and the recess is formed on the other of the inner surface of the first prosthodontic member and the base portion of the second prosthodontic member, the projection being sized, dimensioned, and located relative to the recess to enter and engage the recess when the second prosthodontic member is in the desired position.

30. A prosthodontic assembly as recited in claim 29, in which at least one of the first and second prosthodontic members is made of plastic.

31. A prosthodontic assembly as recited in claim 29, in which both the first and second prosthodontic members are made of plastic.

32. A prosthodontic assembly as recited in claim 28, in which at least one of the first and second prosthodontic member is injection molded out of plastic.

33. A prosthodontic assembly as recited in claim 28, in which the first prosthodontic member is an abutment member.

34. A prosthodontic assembly as recited in claim 33, in which the bore extends through the abutment member.

35. A prosthodontic assembly as recited in claim 33, in which the fastener is a screw member and the inner surface of the abutment member further defines a third bore portion for receiving the screw member in a manner that allows the screw member to rotate relative to the abutment member until the screw member engages the inner surface to securely hold the abutment member against the implant member.

36. A prosthodontic assembly as recited in claim 33, in which the first bore portion is adapted to receive a portion of the implant member in a manner that prevents rotation of the abutment member relative to the implant member when the abutment member is attached to the implant member.

37. A prosthodontic assembly as recited in claim 28, in which the first prosthodontic member is a temporary abutment member and the second abutment member is an abutment cap that covers the bore in the temporary abutment member.

38. A prosthodontic assembly as recited in claim 28, in which the second prosthodontic member is an impression member configured to be embedded in impression material.

39. A prosthodontic assembly as recited in claim 28, in which the second prosthodontic member is cast in gold during fabrication of a prosthetic member.

40. A prosthodontic assembly as recited in claim 28, in which the second prosthodontic member is a temporary cylinder.

41. A prosthodontic procedure for forming a dental impression assembly used to fabricate a prosthetic member for a patient, the procedure comprising the steps of:
   providing an implant member having an upper surface and an internal surface defining an internal cavity, where the internal surface intersects the upper surface such the internal cavity communicates with the exterior through the upper surface;
   placing the implant member into the patient's jaw bone;
   providing an impression member having a base portion and an impression portion, where the base portion comprises a lower post sized and dimensioned to be snugly received within the internal cavity of the implant member;
   attaching the impression member to the implant member by inserting the lower post of the impression member into the internal cavity of the implant member to form a friction fit that inhibits removal of the impression member from the implant member;
   embedding the impression portion of the impression member in impression material;
   allowing the impression material to harden to form the impression assembly; and
   applying deliberate force to the hardened impression material to displace the impression assembly from the implant member.

42. A procedure as recited in claim 41, in which the step of providing the implant member further comprises the step of threading the internal cavity.

43. A procedure as recited in claim 41, further comprising the steps of:
   attaching an implant analog to the impression member;
   embedding the implant analog in model material; and
   allowing the model material to harden to form a model of the patient's mouth.

44. A procedure as recited in claim 41, further comprising the steps:
   forming the implant member of metal; and
   forming the impression member of plastic.

* * * * *